United States Patent
Riebel

(10) Patent No.: US 8,696,998 B2
(45) Date of Patent: Apr. 15, 2014

(54) BIOOPTICAL AND BIOFUNCTIONAL PROPERTIES, APPLICATIONS AND METHODS OF POLYLACTIC ACID FILMS

(75) Inventor: Michael J. Riebel, Mankato, MN (US)

(73) Assignee: Green Bubble Technologies LLC, Mankato, MN (US)

(*) Notice: Subject to any disclaimer, the term of this patent is extended or adjusted under 35 U.S.C. 154(b) by 210 days.

(21) Appl. No.: 13/183,140

(22) Filed: Jul. 14, 2011

(65) Prior Publication Data

US 2012/0014845 A1 Jan. 19, 2012

Related U.S. Application Data

(60) Provisional application No. 61/364,306, filed on Jul. 14, 2010.

(51) Int. Cl.
*B01J 19/08* (2006.01)
(52) U.S. Cl.
USPC ................................................ 422/186.3
(58) Field of Classification Search
USPC ...................................................... 422/186.3
See application file for complete search history.

(56) References Cited

U.S. PATENT DOCUMENTS

| | | | |
|---|---|---|---|
| 3,367,917 A | 2/1968 | Granito | |
| 3,407,154 A | 10/1968 | Casebolt et al. | |
| 5,082,605 A | 1/1992 | Brooks et al. | |
| 5,088,910 A | 2/1992 | Goforth et al. | |
| 5,096,046 A | 3/1992 | Goforth et al. | |
| 5,474,722 A | 12/1995 | Woodhams | |
| 5,480,602 A | 1/1996 | Nagaich | |
| 5,516,472 A | 5/1996 | Laver | |
| 5,593,625 A | 1/1997 | Riebel et al. | |
| 5,636,123 A | 6/1997 | Rich et al. | |
| 5,827,462 A | 10/1998 | Brandt et al. | |
| 5,863,480 A | 1/1999 | Suwanda | |
| 5,866,264 A | 2/1999 | Zehner et al. | |
| 5,882,774 A | 3/1999 | Jonza et al. | |
| 5,919,422 A * | 7/1999 | Yamanaka et al. | 422/121 |
| 5,952,105 A | 9/1999 | Medoff et al. | |
| 5,973,035 A | 10/1999 | Medoff et al. | |
| 6,011,091 A | 1/2000 | Zehner | |
| 6,117,924 A | 9/2000 | Brandt | |
| 6,207,729 B1 | 3/2001 | Medoff et al. | |
| 6,758,996 B2 | 7/2004 | Monovoukas et al. | |
| 6,924,014 B2 | 8/2005 | Ouderkirk et al. | |
| 7,297,394 B2 | 11/2007 | Khemani et al. | |
| 7,615,275 B2 | 11/2009 | Foerg et al. | |
| 2003/0165702 A1 | 9/2003 | Disse et al. | |
| 2005/0241759 A1 | 11/2005 | Goodson et al. | |
| 2006/0199729 A1 | 9/2006 | Naganuma et al. | |
| 2008/0134939 A1 | 6/2008 | Arpac et al. | |
| 2009/0275464 A1 * | 11/2009 | Horiuchi et al. | 502/159 |

FOREIGN PATENT DOCUMENTS

| | | |
|---|---|---|
| CA | 2278688 A1 | 6/1999 |
| GB | 2473727 A | 3/2011 |
| WO | 2011012935 A2 | 2/2011 |

OTHER PUBLICATIONS

Ooka et al. "Prevention of photocatalytic deterioration of resins using T102 pillared fluoromica", Applied Clay Science, Elsevier Science, vol. 42, No. 3-4, pp. 363-367 (Jan. 1, 2009).
International Search Report for related PCT Application No. PCT/US2011/045084 mailed Apr. 20, 2012 (7 pp.).
International Search Report for related PCT Application No. PCT/US2011/044035 mailed Sep. 7, 2011 (4 pp.).

* cited by examiner

*Primary Examiner* — Kishor Mayekar
(74) *Attorney, Agent, or Firm* — Winthrop & Weinstine, P.A.

(57) ABSTRACT

High surface energy materials with low refractive index and UV transparency wherein multilayers of similar or dissimilar materials are thermally fused together to form various functional optical requirements are provided. In some embodiments, a photocatalytic biopolymer system comprising of a UV transparent biopolymer in integrating fused nanophotocatalytic minerals such as Tio2 used for various applications is provided. Many embodiments are based on the integration of nanophotocatalytic minerals fused to a biopolymer system in which the biopolymer system is UV transparent (UVT) and allows UV light to be transmitted through the biopolymer system activating the nanophotocatalytic fused layer.

10 Claims, No Drawings

BIOOPTICAL AND BIOFUNCTIONAL PROPERTIES, APPLICATIONS AND METHODS OF POLYLACTIC ACID FILMS

This application claims priority to U.S. Provisional Application No. 61/364,306, filed Jul. 14, 2010, the content of which is hereby incorporated in its entirety by reference.

BACKGROUND

Photocatalytic Reactions

In chemistry, photocatalysis is the acceleration of a photo-reaction in the presence of a catalyst. In catalysed photolysis, light is absorbed by an adsorbed substrate. In photogenerated catalysis, the photocatalytic activity (PCA) depends on the ability of the catalyst to create electron-hole pairs, which generate free radicals (hydroxyl radicals: .OH) able to undergo secondary reactions. Its comprehension has been made possible ever since the discovery of water electrolysis by means of the titanium dioxide. Commercial application of the process is called Advanced Oxidation Process (AOP). There are several methods of achieving AOP's, that can but do not necessarily involve TiO2 or even the use of UV light. Generally the defining factor is the production and use of the hydroxyl radical The principle of photocatalytic reaction was to accelerate the nature's cleaning and purifying process using light as energy. Discovered in 1960's, Dr. Fujishima of Japan found titanium metal, after irradiated by light, could break water molecule into oxygen and hydrogen gas. By restructuring titanium dioxide particles in nano-scale, a number of new physical and chemical properties were discovered. One of these newfound effects was photocatalytic oxidation which accelerated the formation of hydroxyl radical, one of the strongest oxidizing agents created by nature. Using energy found in the UV light, photocatalyst titanium dioxide could breakdown numerous organic substances such as oil grime and hydrocarbons from car exhaust and industrial smog, volatile organic compounds found in various building materials and furniture, organic growth such as fungus and mildew. In addition to its photocatalytic oxidation effect, titanium dioxide coating also exhibited hydrophilic property (or high water-affinity) which titanium dioxide coating attracted water moist in the air to form an invisible film of water. This thin film of water allowed the substrate to be anti-static so the coated surface could be easily cleaned by rinse of water. For years, titanium dioxide was used in many commodity products such as paint, cosmetics, sun blocks, and etc. It is a safe and stable substance commonly found in our lives. Numerous applications have been developed from utilizing photocatalytic reaction.

When photocatalyst titanium dioxide (TiO2) absorbs Ultraviolet (UV) radiation from sunlight or illuminated light source (fluorescent lamps), it will produce pairs of electrons and holes. The electron of the valence band of titanium dioxide becomes excited when illuminated by light. The excess energy of this excited electron promoted the electron to the conduction band of titanium dioxide therefore creating the negative-electron (e−) and positive-hole (h+) pair. This stage is referred as the semiconductor's 'photo-excitation' state. The energy difference between the valence band and the conduction band is known as the 'Band Gap'. Wavelength of the light necessary for photo-excitation is: 1240 (Planck's constant, h)/3.2 ev (band gap energy)=388 nm The positive-hole of titanium dioxide breaks apart the water molecule to form hydrogen gas and hydroxyl radical. The negative-electron reacts with oxygen molecule to form super oxide anion. This cycle continues when light is available Photocatalytic oxidation is achieved when UV light rays are combined with a TiO2 coated filter. TiO2 refers to Titanium Dioxide. This process creates hydroxyl radicals and super-oxide ions, which are highly reactive electrons.

These highly reactive electrons aggressively combine with other elements in the air, such as bacteria and VOCs. VOC is an acronym for Volatile Organic Compounds which include harmful pollutants such as formaldehyde, ammonia and many other common contaminants released by building materials and household cleaners generally found in the home. Effective oxidation of the pollutants breaks down into harmless carbon dioxide and water molecules, drastically improving the air quality.

Biopolymers

With growing environmental concerns over petrochemical products and its environmentally harmful practices, new environmentally friendly polymers being developed as a replacement for petrochemical based plastics. Materials such as PLA (polylactic acid) such as product produced by Natureworks (Cargill) are derived from natural and rapidly renewable resources of corn. To date the vast majority of interest and commercialization is the application of PLA for disposable packaging and other disposal products. Although thought of as a disposable plastic, PLA has many new abilities and functions that can further expand the usage of this environmentally friendly biobased technology.

Polylactic acid is not derived from petrochemical materials, but from the conversion of starch or cellulosic materials into dextrose then into a lactic acid. The lactic acid is then polymerized into a range of polymer products. This conversion process has been documented and is currently commercialized. Being that PLA is not petrochemical based, it has other unique functional and processing abilities outside that of petrochemicals that provides unique optical and functional properties outside of the needs for basic disposable packaging.

Plastics typically block UV such as acrylic, polystyrene, PE, PP and most all petrochemical plastics. Currently fused quartz mineral is used for UV transparent applications, but is both difficult and expensive to shape or form into shapes. Secondly quartz mineral cannot be easily soften to fuse nanominerals onto its surface. Currently few materials are UV transparent and most are expensive or classified as a hazardous material. Traditionally material such as quartz or sapphire have been used in some of these industries providing a high degree of UV stability. These material have limitations in cost, fabrication, and other limitations. Other engineered polymers such as fluoropolymers have been used in UV transparent applications, but are hindered by cost and health considerations. Law suits have been won suing company's based on fluoropolymers emissions and pollution.

PLA is a thermoplastic polyester derived from field corn of 2-hydroxy lactate (lactic acid) or lactide. The formula of the subunit is: —[O—CH(CH3)—CO]— The alpha-carbon of the monomer is optically active (L-configuration). The polylactic acid-based polymer is typically selected from the group consisting of D-polylactic acid, L-polylactic acid, D,L-polylactic acid, meso-polylactic acid, and any combination of D-polylactic acid, L-polylactic acid, D,L-polylactic acid and meso-polylactic acid. In one embodiment, the polylactic acid-based material includes predominantly PLLA (poly-L-Lactic acid). In one embodiment, the number average molecular weight is about 140,000, although a workable range for the polymer is between about 15,000 and about 300,000. In one embodiment, the PLA is L9000™ (Biomer, Germany), apolylactic acid)

Polylactic acid is a relatively high specific gravity as compared to common plastics with a specific gravity closer to engineered plastics such as Polycarbonate. Although similar in specific gravity to polycarbonate used in various functional arid optical products, PLA has a much lower refractive index. In addition due to the unique molecular structure and materials, PLA is virtually transparent in UV wavelength spectrum as compared to polycarbonate and other common plastics that have very high UV absorption rates. From this PLA does not have visible or UV degradation or yellowing as found in common plastics. UV transparency and a low refractive index can have a myriad of applications.

UV Resistance and UV Transparency

It has been discovered the PLA has very good UV resistance in regards to UV degradation. Various tests have been performed in UV weatherometers showing that PLA does not yellow when exposed to exterior light. In addition, tests based on UV-visible photospectrometers show that PLA is transparent the UV A, UV B, and in most of the UV C ranges. This shows that the material allows full transmission of UV waves.

Other materials such as polycarbonate have high degrees of clarity in the visible light spectrum but have high degrees of UV absorption. Most polymers are carefully measured for their UV absorption due to the fact that the absorption of UV has a significant relationship to UV degradation of the polymers. Polymers are vary greatly in their resistance to weathering, such as polymethylathacrylate (PMMA) and polytetrafluosoethylene (PTFE) are transparent to UV radiation and hence not susceptible to photodegradation. Materials such as PTFE and PMMA are considered "UV Transparent" materials According to data obtained, the following show a specific wavelength wherein the material starts to absorb UV-visible wavelengths:

|  |  |
|---|---|
| PET | 420 nm |
| Polycarbonate | 330 nm |
| PLA | 240 nm |

UV or ultra violet radiation is a shorter wavelength than visible light spectra. The following represents the areas of various UV energy classifications:

| UV A | Long wave (black light) | 315 to 400 nm |
|---|---|---|
| UV B | UB Medium wave | 280 to 315 nm |
| UV C | Short wave (germicidal) | 100 to 280 |

From the above chart reference, it can be seen that PLA starts absorption at a much shorter UV wavelength and in addition the amount of absorption is lower than that of a high quality PET that significantly lower than a polycarbonate material.

PLA also is unique in the fact that it has a high surface energy. PLA has a similar range of refractive index as Fluoropolymers, but with much higher surface energy.

Little work has been found in the areas of measurement of various optical, electrical or other functional performance of PLA and various methods of hybridizing PLA with the addition or various additives, chemicals or nanomaterials.

Polylactic acid has a specific gravity typically around the 1.25 range and can produced in a transparent form. Common plastics for optical and other functional applications such as polycarbonate have specific gravities of typically 1.2 to 1.22.

The optical nature of petrochemicals is known and used for many applications including eyewear lens, television display screen s, protective coatings and myriad other optical applications.

Optical properties such as refractive index, UV absorption/transmission and UV resistance are important issues related to optical properties within petrochemical polymers used in optical applications.

Refractive Index

The refractive index or index of refraction is a ratio of the speed of light in a vacuum relative to that speed through a given medium (this quantity does not refer to an angle of refraction, which can be derived from the refractive index using Snell's Law). In other words, as light passes from one medium to another as from air to water, the result is a bending of light rays at an angle. This physical property occurs because there is a change in the velocity of light going from one medium into another. Refractive index also describes the quantity that light is bent as it passes through a single substance. This involves calculating the angle at which light enters the medium and comparing that with the angle at which the light leaves the medium.

Another view rates each substance with its own refractive index. This is because the velocity of light through the substance is compared as a ratio to the velocity of light in a vacuum. The velocity at which light travels in a vacuum is a physical constant, and the fastest speed at which energy or information can travel. However, light travels slower through any given material, or medium, that is not a vacuum. This is actually a delay from when light enters the material to when it leaves; i.e., when some is absorbed, and another part transmitted. The following shows various refractive indices of plastics:

| Specific Gravity | Refractive Index |
|---|---|
| Polycarbonate 1.2-1.22 | 1.58 |
| Polylactic Acid 1.24-1.25 | 1.46 note: Range with blending (1.4 to 1.55) |

The difference of refractive index between PLA and conventional petrochemical polymers also provides other potential functional features including electrical dielectric strength.

The dielectric constant (which is often dependent on wavelength) is simply the square of the (complex) refractive index in a non-magnetic medium (one with a relative permeability of unity). The refractive index is used for optics in Fresnel equations and Snell's law; while the dielectric constant is used in Maxwell's equations and electronics Thus from this basic physics the dielectric constant of PLA would be lower than conventional petrochemical plastics and have various applications in electrical components and systems.

Fluoropolymers have been investigated for a wide range of innovative optical applications not only because of their possible optical clarity but also because their refractive indices are generally much lower than competing materials such as PMMA and PC. The refractive index for most fluoropolymers is in the region of 1.30 to 1.45 compared with the refractive index for more traditional transparent polymers such as PMMA and PC where it is in the region of 1.5 to 1.6 (or higher). This makes the fluoropolymers suitable for optical technology products such as waveguides, optical filters, fiber gratings and a wide range of optical devices. Specialist ultra-transparent fluoropolymers are also being developed for these applications and for use in rapidly developing CMOS lithography technologies essential for the production of semiconductor devices. The optical clarity and other performance properties of fluoropolymers are opening new markets and opportunities.

The usage of dissimilar materials with various refractive indexes are used for a wide range of applications for antireflective coatings, LCD flat panel screen assemblies, general optical lensing and other similar applications. A lower or different refractive index of PLA in combination with a convention higher refractive index can have unique applications and provide a tool for design of new optical based systems.

Luminous Transmittance

Luminous transmittance for various materials is provided below.

| | |
|---|---|
| Optical glass | 99.9 |
| PMMA | 92 |
| PC | 89 |
| SAN | 88 |
| PS | 88 |
| ABS | 79 |
| PVC | 76 |

SUMMARY

A high surface energy material with low refractive index and UV transparency wherein multilayers of similar or dissimilar materials are thermally fused together to form various functional optical requirements is provided. Various compositions and systems are provided incorporating a UV transparent biopolymer structure are provided. A photocatalytic biopolymer structure comprising of a UV transparent biopolymer in integrating fused nanophotocatalytic minerals such as Tio2 used for various applications is provided. Many embodiments are based on the integration of nanophotocatalytic minerals fused to a biopolymer structure in which the biopolymer structure is UV transparent (UVT) and allows UV light to be transmitted through the biopolymer structure activating the nanophotocatalytic fused layer. A UV Transparent biolamiante either including a photocat within the biolaminate material or as a coating of photocats with various binders are included within the scope of the invention.

DETAILED DESCRIPTION

A high surface energy material with low refractive index and UV transparency wherein multilayers of similar or dissimilar materials are thermally fused together to form various functional optical requirements is provided. Various compositions and systems are provided incorporating a UV transparent biopolymer structure are provided. A photocatalytic biopolymer structure comprising of a UV transparent biopolymer in integrating fused nanophotocatalytic minerals such as Tio2 used for various applications is provided. Many embodiments are based on the integration of nanophotocatalytic minerals fused to a biopolymer structure in which the biopolymer structure is UV transparent (UVT) and allows UV light to be transmitted through the biopolymer structure activating the nanophotocatalytic fused layer. A UV Transparent biolamiante either including a photocat within the biolaminate material or as a coating of photocats with various binders are included within the scope of the invention.

The invention thus provides structures that can be integrated into various products that are 100% "natural" comprising of rapidly renewable biopolymers and natural nanominerals in addition provide an "active device" for the reduction or elimination of bacteria, viruses, VOC's and odor for a wide range of markets.

In some embodiments, a UV transparent biopolymer in the form of a fused particle sheet, extruded sheet, or molded structure wherein the biopolymer structure has fused nanophotocatalytic minerals fused to one surface is provided. The other side of the structure can contain a UV light source such as a fluorescent tube, compact fluorescent light or UV LED in which the UV light is transmitted through the biopolymer structure and activate the nanophotocatalytic fused layer.

In some embodiments, a UV transparent stabilized biopolymer composition, having a high level of UV transmission and UV transmission retention, is provided. The composition is very effective in retaining its UV transmission under various environmental conditions. By UV radiation, as used herein is meant radiation defined in UV-A, UV-B and UV-C spectra typically having a wavelength of 400 nm or shorter, or a light source that contains a certain portion of UV radiation that has a wavelength shorter than 380 nm.

In other embodiments, various forms of UV transparent biopolymer structures including independent fused particle sheets, extruded sheet and molded shapes are provided.

In yet other embodiments, the invention also integrates UV sources from fluorescent lighting tubes, compact fluorescent lighting and UV LED sources. The invention further comprises structures such as fluorescent lighting diffusers and covers.

In still further embodiments, the invention further comprises the combination of a nanophotocatalytic layer in combination with a UV transparent device, structure, lighting covers and diffusers, panel, sheet or film.

The invention further comprises integration of these structures into various devices, products, and applications for reduction of VOC's, air exchanging, bacteria reduction, water purification and other applications. The invention can be used for a wide range of applications, products and devices for the reduction/elimination of bacteria, viruses, VOC's and odor in various markets.

The teachings herein may be widely applied to a variety of fields. The teachings may be used to form films for UV sources, such reflective films including multilayer antireflective films for televisions or other screens and continuous/disperse phase reflective polarizers for screens. Embodiments disclosed herein, including the usage of PLA films of various thicknesses, have use in water treatment films, pipe, conduit and apparatus (UV), germicidal film, solar cell films, medical test containers, and UV photolithography.

Biopolymers

Biopolymer based biolaminates are environmentally friendly and petrochemical free, and also have unique functional features including UV transparency and high degree of resistance to UV degradation. Biopolymer biolaminates are highly polar nature also provide a high degree of ability to load various levels of fillers or functional materials such as photocatalytic particles or nanoparticle or blends thereof. The UV transparency and resistance of UV degradation provides unique properties for photocatalytic materials such as nano Tio2 and other similar forms of nanophotocatalytic materials.

PLA has a higher specific gravity but a lower refractive index compared to polycarbonates.

| Specific Gravity | Refractive Index |
| --- | --- |
| Polycarbonate 1.2-1.22 | 1.58 |
| Polylactic Acid 1.24-1.25 | 1.46 note: Range with blending (1.4 to 1.55) |

Polylactic acid can be modified with various biobased additives and various petrochemical additives to "adjust" various functional and optical properties. Examples include, but are not limited to: acrylics, polycarbonates, silicon, fluorine based chemistry, standard petrochemical plastics, UV functional additives, nanomaterials and other such modifiers. Although these embodiments are based on the usage of PLA, the addition of small portions of these other additives or modifiers can be used to make adjustments in these various optical, electrical or functional properties.

Because of its UV Transparency, PLA does not substantially degrade based on exposure to UV light or exterior sunlight containing UV spectra. Photo-degradation in plastics is caused by the UV component of solar radiation, that is radiation of wavelength from 0.295 to 0.400 nm. This is absorbed by some plastics and causes the breakage of bonds in the polymers leading to photo-oxidation. Being PLA is transparent at a broader range of UV wavelengths, PLA is not susceptable to this form of molecular bond breakageés leading to yellowing or photodegradation.

PLA is unique to have a lower refactive index, with a high specific gravity, UV transparency and low UV degradation. In addition the ability to modify PLA by means of processing or by compounding of additives will show that these forms of functional PLA can have broad ranging application for optical, electrical and functional applications.

Various waxes such as Carnuba wax are compatitible with PLA and match refractive index. Carnuba wax has a refractive index of 1.45. Other material or waxes such as a soybean oil wax or "hydrogenated oil" based wax also provides a lower or matching refractive index.

PLA has a similar range of refractive index as Fluoropolymers and is equal or better in UV transmission based on the PLA formulation or PLA composite makeup. Polylactic acid as a specific gravity typically around the 1.25 range and can produced in a transparent form. Common plastics for optical and other functional applications such as Polycarbonate have specific gravities of typically 1.2 to 1.22 but are UV opaque.

PLA's current refractive index of 1.4 is within the upper range of the fluoropolymers. With "biomodification" and additives, PLA's refractive index may be maipulated within a similar range.

Biopolymers have a unique ability to be "UV Transparent" at UV wavelengths primarily in the UV spectra and at the 388 nm at the primary wavelength of the TiO2 photocatyst optimal performance range. Secondly, the polar nature of the biolaminate primary biopolymer also can include other functional minerals such as natural quartz or other minerals that are also UV transparent.

The biopolymer structure can include fillers or additives that are also UV transparent as not to decrease the efficiency of UV transmission that drives the photocatatlyic reaction. Fillers such as nanoquartz, fused silica, fluoropolymers, or particles of fluoropolymers and specialized acrylics can be blended with the biopolymer as long as they also have similar UV transparency characteristics as the UV transparent biopolymer.

While polylactic acid (PLA) is specifically discussed herein, other biopolymers having similar UV transparency, for example cellulose acetate, may alternatively be used.

Materials of low refractive index or UV transparent are typically expensive and difficult polymeric films. In many cases such as in fluorinated polymer used for AR, these polymers and the common addition of silicon reduces the surface energy of the film where adhesion to dissimilar material is difficult.

The unique refractive index of PLA is closely matched to that of the above art. The above art has limitation in regards to adhesion. PLA also has a unique surface energy averaging about 40 DYNE and can be easily modified. This surface energy level is optimal for printing and adhesion while still providing a low refractive index and UV transparency.

PLA Summary

Polylactic acid is a relatively high specific gravity as compared to common plastics with a specific gravity closer to engineered plastics such as Polycarbonate. Although similar in specific gravity to polycarbonate used in various functional and optical products, PLA has a much lower refractive index. In addition due to the unique molecular structure and materials, PLA is virtually transparent in UV wavelength spectrum as compared to polycarbonate and other common plastics that have very high UV absorption rates. From this PLA does not have visible or UV degradation or yellowing as founding common plastics.

PLA also is unique in the fact that it has a high surface energy that promotes the ability to coat the material with various optical coatings such as antireflective, photochromic, and other coating methods for optical materials and products. PLA surface energy is typically 40 Dyne and can be further modified by corona treatments and other means to change surface energy.

Spectraphotometry tests show that polylactic acid is UV transparent and provides additional optical properties in the visible and UV spectra. The ability to integrate UV transparent mineral, nanominerals and other UV transparent polymers provides the ability to create new materials, devices, and products that meet the need for UV transparency and provide an environmentally friendly solution. This invention of UV transparent biopolymers or biocomposites also can be molded, postformed, or shaped into complex shapes that are difficult to produce using quartz.

In some embodiments, modifications to the refractive index of PLA are provided. Such modifications may be done using a wax, wherein the wax has a refractive index at or below 1.45. Alternatively, such modifications may be done using acrylates wherein the polymer blend can have a modified UV transparency and refractive index. To better match the refractive index of PLA, low Tg acrylics such as ethyl acrylate or butyl acrylate may be used.

Titanium Dioxide

TiO2, titanium dioxide, or titania is the naturally occurring oxide of titanium and is known for the stability of its chemical structure, its biocompatibility and physical, optical and electrical properties. Titanium dioxide occurs in nature as the well-known naturally occurring minerals rutile, anatase and brookite. Zinc oxide and Titanium dioxide, particularly in the anatase form, are photocatalysts under ultraviolet light This has been discussed for example in the report from Maness et al (Maness et al, Applied and Environmental Microbiology, 65, (1999) 4094-8). Recently, it has been found that titanium dioxide, when spiked with nitrogen ions, is also a photocatalyst under visible light Titanium dioxide is a photocatalyst when irradiated with light The light is absorbed by the oxide material triggering a chemical reaction that, in the presence of water, ends with the oxidation of water to create hydroxyl radicals. The reaction can also produce oxygen radicals or even oxidize organic materials directly Moreover, free radicals actively modulate immune responses, activate macrophages and stimulate the healing process $TiO_2$ is a potent photocatalyst that can break down almost any organic compound when exposed to sunlight and be used for water and air treatment as well as for catalytic production of gases. The general scheme for the photocatalytic destruction of organics begins with its excitation by suprabandgap photons, and continues through redox reactions where OH radicals, formed on the photocatalyst surface, play a major role.

Photocatalysts

Photocatalysts, upon activation or exposure to sunlight, establish both oxidation and reduction sites. These sites are capable of preventing or inhibiting the growth of algae on the substrate or generating reactive species that inhibit the growth of algae on the substrate. In other embodiments, the sites generate reactive species that inhibit the growth of biota on the substrate. The sites themselves, or the reactive species generated by the sites, may also photooxidize other surface contaminants such as dirt or soot or pollen. Photocatalytic elements are also capable of generating reactive species which react with organic contaminants converting them to materials which volatilize or rinse away readily. Photocatalytic particles conventionally recognized by those skilled in the art are suitable for use with the present invention. Suitable photocatalysts include, but are not limited to, $TiO_2$, $ZnO$, $WO_3$, $SnO_2$, $CaTiO_3$, $Fe_2O_3$, $MoO_3$, $Nb_2O_5$, $Ti_xZr_{(1-x)}O_2$, $SiC$, $SrTiO_3$, $CdS$, $GaP$, $InP$, $GaAs$, $BaTiO_3$, $KNbO_3$, $Ta_2O_5$, $Bi_2O_3$, $NiO$, $Cu_2O$, $SiO_2$, $MoS_2$, $InPb$, $RuO_2$, $CeO_2$, $Ti(OH)_4$, combinations thereof, or inactive particles coated with a photocatalytic coating. In other embodiments, the photocatalytic particles are doped with, for example, carbon, nitrogen, sulfur, fluorine, and the like. In other embodiments, the dopant may be a metallic element such as Pt, Ag, or Cu. In some embodiments, the doping material modified the bandgap of the photocatalytic particle. In some embodiments, the transition metal oxide photocatalyst is nanocrystalline anatase $TiO_2$ Nanometer photocatalyst may be made from $TiO_2$ grains, the sizes of which are under 20 nm. After they absorb UV in sunshine and illuminate lamp-house, the electrons on them are activated by UV and flies off, then produce electron holes, which have strong oxidation ability (the holes are produced, when the electrons are flying off). The electron has strong deoxidization ability, will produce oxidation anion free radicals and oxyhydrogen free radicals after reacting with $H_2O$ and $O_2$ in air. They have strong oxidation ability, and can decompose the organic, contaminants, fume, and bacteria into hurtles $CO_2$ and $H_2O$. At the same time, the electrons make deoxidization reaction to deoxidize the oxygen in air Photocatalysts have strong efficacy in preventing mildew. The cloth packaged food utilizing photocatalyst can obviously suppress going mould. It can keep fresh in 10 days. According to the experiments, the efficacy spraying over 1000 square meters is equivalent to the air purifying ability of 70 silver birch.

Photocatalyst Nano-$TiO_2$ super disinfections power has been verified to kill bacteria, virus and fungi, as well as to eliminate foul smell. It has been tested with a series of experiences by different authorities and academic bodies, Food Research Center, Universities, etc, and having very good performance. Photocatalyst. Nano-$TiO_2$ can kill Pseudomonas aeruginosa, Influenza virus, MRSA, Tubercle Bacillus, etc. Photocatalyst Nano-$TiO_2$ also has been tested and can eliminate the toxic and carcinogen gases, such VOC and formaldehyde, etc.

The threshold wavelength for titanium dioxide photocatalyst is 388 nm. At wavelengths below that the outer valence electron in the $TiO_2$ molecule simply needs to absorb enough photons to have the energy to escape.

The invention also includes various photocatalytic minerals that are doped. This may further increase the efficiencies of the devices and systems within this invention by increasing the light wavelength range from UV as to also include lower ends of the visible light spectra. Although covered within this invention, the preferred means is photocatalytic minerals that operate in the UV spectra.

UV Transparent Composites

UV Transparent (UVT) biopolymer composites are provided herein. The UVT biopolymer material within this invention may be blended with various fillers, fibers, minerals, additives, and polymer blends as long as they do not significantly limit the UV transparent function of the UVT biopolymer. These materials can modify the mechanical or physical performance of the final product or device for specific applications requirements.

Fillers such as quartz, ATH and other UVT minerals can be compounded with the UVT Biopolymer to increase its stiffness and improve heat resistance while having minimal effect on the UVT properties.

Fiber reinforcement can also be integrated into the material including glass fibers, mineral fibers, certain natural fibers and other common forms of fiber reinforcement to improve the mechanical properties of the final shape, sheet or panel.

Other petrochemical polymer additives can also be added such as fluropolymers, and special acrylics that also have similar UVT properties.

Applications

A PLA film may be used as an anti-reflective film for screens, such as television screens, and provides an interface between current petrochemical screen films and air. In one embodiment, an assembly is provided wherein a low refractive index PLA is extruded into a film and used within a multilayer assembly for television screens. One application is related to that of continuous/disperse phase reflective polarizers used in LCD televisions that rely on the difference in refractive index between at least two materials, usually polymeric materials, to selectively reflect light of one polarization state while transmitting light in an orthogonal polarization state. In one embodiment, an assembly of a thin PLA film in combination with a optical grade plastic or glass wherein the refractive index of the PLA is lower and provides a AR coating is provided.

With the design considerations described in U.S. Pat. No. 5,882,774, one of ordinary skill will readily appreciate that a wide variety of materials can be used to form multilayer polymeric reflective mirror films when processed under conditions selected to yield the desired refractive index relationships. The desired refractive index relationships can be achieved in a variety of ways, including stretching during or after film formation (e.g., in the case of organic polymers), extruding (e.g., in the case of liquid crystalline materials), or coating. In addition, it is preferred that the two materials have similar rheological properties (e.g., melt viscosities) such that they can be co-extruded.

Antireflective Coatings

An antireflective or anti-reflection (AR) coating is a type of optical coating applied to the surface of lenses and other optical devices to reduce reflection. This improves the efficiency of the system since less light is lost. In complex systems such as a telescope, the reduction in reflections also improves the contrast of the image by elimination of stray light. This is especially important in planetary astronomy. In other applications, the primary benefit is the elimination of the reflection itself, such as a coating on eyeglass lenses that makes the eyes of the wearer more visible to others, or a coating to reduce the glint from a covert viewer's binoculars or telescopic sight.

Many coatings consist of transparent thin film structures with alternating layers of contrasting refractive index. Layer thicknesses are chosen to produce destructive interference in the beams reflected from the interfaces, and constructive interference in the corresponding transmitted beams. This makes the structure's performance change with wavelength and incident angle, so that color effects often appear at oblique angles. A wavelength range must be specified when designing or ordering such coatings, but good performance can often be achieved for a relatively wide range of frequencies: usually a choice of IR, visible, or UV is offered The simplest interference AR coating consists of a single quarter-wave layer of transparent material whose refractive index is the square root of the substrate's refractive index; this, theoretically, gives zero reflectance at the center wavelength and decreased reflectance for wavelengths in a broad band around the center.

The most common type of optical glass is crown glass, which has an index of refraction of about 1.52. An optimum single layer coating would, have to be made of a material with an index equal to about 1.23. Unfortunately, there is no material with such an index that has good physical properties for an optical coating. The closest 'good' materials available are magnesium fluoride, MgF2 (with an index of 1.38), and fluoropolymers (which can have indices as low as 1.30, but are more difficult to apply). MgF2, on a crown glass surface, and bare glass give reflectances of about 1% and 4%, respectively. MgF2 coatings perform much better on higher-index glasses, especially those with index of refraction close to 1.9. MgF2 coatings are commonly used because they are cheap, and when they are designed for a wavelength in the middle of the visible band they give reasonably good anti-reflection over the entire band Antireflective polymer films ("AR films"), or AR coatings, are becoming increasingly important in the display industry. New applications are being developed for low reflective films and other AR coatings applied to articles used in the computer, television, appliance, mobile phone, aerospace and automotive industries.

AR films are typically constructed by alternating high and low refractive index polymer layers in order to minimize the amount of light that is reflected. Desirable features in AR films for use on the substrate of the articles are the combination of a low percentage of reflected light (e.g. 1.5% or lower) and durability to scratches and abrasions. These features are obtained in AR constructions by maximizing the delta RI between the polymer layers while maintaining strong adhesion between the polymer layers.

The low refractive index polymer layers used in AR films are usually derived from fluorine containing polymers ("fluoropolymers" or "fluorinated polymers"), which have refractive indices that range from about 1.3 to 1.4. Fluoropolymers provide unique advantages over conventional hydrocarbon based materials in terms of high chemical inertness (in terms of acid and base resistance), dirt and stain resistance (due to low surface energy), low moisture absorption, and resistance to weather and solar conditions.

The refractive index of fluorinated polymer coating layers is dependent upon the volume percentage of fluorine contained within the layers. Increased fluorine content decreases the refractive index of the coating layers.

However, increasing the fluorine content also decreases the surface energy of the coating layers, which in turn reduces the interfacial adhesion of the fluoropolymer layer to the other polymer or substrate layers to which the layer is coupled.

Other materials investigated for use in low refractive index layers are silicone-containing polymeric materials. Silicone-containing polymeric materials have generally low refractive indices. Further, silicone-containing polymeric coating layers generally have higher surface energies than fluoropolymer-base layers, thus allowing the silicone-containing polymeric layer to more easily adhere to other layers, such as high refractive index layers, or substrates. This added adhesion improves scratch resistance in multilayer antireflection coatings. However, silicone-containing polymeric materials have a higher refractive index as compared with fluorine containing materials. Further, silicone-containing polymeric materials have a lower viscosity that leads to defects in ultra-thin coatings (less than about 100 nanometers).

Thus, it is highly desirable to form a low refractive index layer for an antireflection film having increased fluorine content, and hence lower refractive index, while improving interfacial adhesion to accompanying layers or substrates.

Accordingly, an antireflective coating using PLA as described herein may be used.

Optical Mirror Films

Multilayer optical mirror films as used in conjunction with the present invention exhibit relatively low absorption of incident light, as well as high reflectivity for off-axis as well as normal light rays. The unique properties and advantages of the multi-layer optical film provides an opportunity to design highly efficient backlight systems which exhibit low absorption losses when compared to known backlight systems. Exemplary multilayer optical mirror film of the present invention is described in U.S. Pat. No. 6,924,014, which is incorporated herein by reference (see Example 1 and Example 2). Exemplary multilayer optical mirror film includes a multilayer stack having alternating layers of at least two materials. At least one of the materials has the property of stress induced birefringence, such that the index of refraction (n) of the material is affected by the stretching process. The difference in refractive index at each boundary between layers will cause part of ray to be reflected. By stretching the multilayer stack over a range of uniaxial to biaxial orientation, a film is created with a range of reflectivities for differently oriented plane-polarized incident light. The multilayer stack can thus be made useful as a mirror. Multilayer optical films constructed accordingly exhibit a Brewster angle (the angle at which reflectance goes to zero for light incident at any of the layer interfaces) which is very large or is nonexistent. As a result, these polymeric multilayer stacks having high reflectivity for both s and p polarized light over a wide bandwidth, and over a wide range of angles, reflection can be achieved.

UVT PCO Coated Panel or Film

A UVT biopolymer can be extruded into the form of a sheet or film which then can be coated using various optical coating methods such as antireflective, photochomic, refective and other coatings commonly used in optical coatings. The photocatalytic materials can be either integrated into these coating layers or applied separately over the surface of the optical coatings. In one embodiment, an assembly wherein a UV Transparent PLA film is extruded into a film or tube used for germicidal UV apparatus is provided.

Lighting Diffuser

Commercial ceiling fluorescent lighting fixtures currently use plastic acrylic or polystyrene covers or diffuser panels to protect the bulb if broken and to disperse the light more uniformly within a room. Both acrylic and polystyrene are opaque or block UV spectra. The invention integrates a sheet or UVT embossed structure as a direct replacement for the diffuser. A nanophotocatalytic coating or fused layer of nanominerals are fused to one side of the structure. The UV source in the form of a fixed fluorescent, UV led or other UV lighting sources are on the alternate side allowing the UV spectra to be efficiently transmitted through the UVT structure activating the nanophotocatalytic layer. The resulting light panel can be installed in standard commercial ceiling fixtures for new or remodel construction and provide bacteria, virus, VOC and odor reduction for facilities.

A UVT PCO lighting diffuser comprises of a panel either extruded, molded or of fused particles into standard dropped ceiling lighting covers sizes. The panel is coated with a PCO layer and the panel can be reheated to fuse the nanoparticles onto the surface. The UVT panel can also include transparent colored particles for aesthetic and branding recognition. The panel can also include decorative inclusion including recycled glass, fibers and minerals as long as they do not significantly reduce the UV Transparent function of the panel. The UVT PCO lighting diffuser has various embossed or molded textures as to better improve the light diffusion.

VOC Exchanger Devices

The UVT panels coated with a nanophotocatalytic layer in which a UV light source passes through the UVT panel to activate the nanophotocatalytic layer can be designed in various air exchanger devices. Flat or molded UVT biopolymer panels are extruded, molded or postformed into panels that are placed inside of an air enclosure. Air is blown or pulled through the enclosure by means of a fan. A UV source is placed on the side or outside of the enclosures wherein UV light can penetrate into the enclosure. Multiple panels of the UVT biopolymer nanocoated panels line up as to allow linear laminar flow through the enclosure without restriction. The UV light from the side or outside of the enclosure penetrates to the first UVT PCO panel and UV light will continue to pass through reaching the next panel. This allow for a multiple panels to be stacked to increase surface area and efficiencies within the enclosure for the reduction of VOCs, bacteria and odor. The device can also include a filter mechanism.

This mechanism or device can be built as a stand alone VOC exchanger wherein it recycles the air within a room. This also can be designed to fit within exhaust pipes to remove VOC's prior to being emitted to the outside environment.

UVT PCO Window Film.

A thin film of a UVT biopolymer is extruded using standard film extrusion methods. Other UVT materials, fillers, additives, tints, colorants, plasticizers and processing aides can be added as long as they do not significantly reduce the UV transparent function of the film. After extrusion the film is coated with a PCO material layer and optionally reheated to fuse the nanoparticles of the PCO onto the UVT biopolymeric film. The film can also be secondary coated with various antireflective or optical coatings. The film also can comprise of an window adhesive layer for window film applications again as long as the adhesive has minimal effect on the UV transparency of the UVT biopolymer film.

UVT PCO Water Purification Device and Hydrogen Generation.

A UVT biopolymer tube shape structure can be made from extrusion or postforming. A PCO coating is fused to the inside of the tube and a UV source mounted on the outside of the tube. Water flowing through the tube is processed by means of the nanophotocatalytic and residual UV light spectra that also can act as a germicide. Modifications to this structure may also have applications for the generation of Hydrogen as a renewable fuel. The device would utilize both direct sunlight and a separate UV light source underneath the UVT/PCO biopolymer layer in which water can be stored and converted into hydrogen.

UVT PCO Molded Device

A UVT PCO molded device comprises of a injection molded UVT biopolymer wherein a UV or full spectra including UV source can be inserted into the middle or center of the molded device. A nanophotocatalytic layer is applied and fused to the outside surface of the molded device. The device can be used in various applications for clothing, shoes, textiles, water purification, and medical devices for the reduction of VOC, odor, bacteria and viruses.

UV Crosslinking Applications

The potential of "UV TRANSPARENT" has other potential applications in coatings wherein UV curing technology may have applications. One example would be wherein a molten PLA blended with a photoinitiator would be extruded and subjected to UV curing to obtain crosslinking.

Fluorescent Lighting

Fluorescent bulbs commonly used in drop ceiling lighting fixtures residual UV spectra provides sufficient UV source to activate the photocatylitic surface through the UV transparent structure or device. A fluorescent lamp or fluorescent tube is a gas-discharge lamp that uses electricity to excite mercury vapor. The excited mercury atoms produce short-wave ultraviolet light that then causes a phosphor to fluoresce, producing visible light. A fluorescent lamp converts electrical power into useful light more efficiently than an incandescent lamp. While larger fluorescent lamps have been mostly used in commercial or institutional buildings, the compact fluorescent lamp is now available in the same popular sizes as incandescents and is used as an energy-saving alternative in homes. The phosphor fluoresce process is not 100% efficient and thus a percentage of UV light is emitted from common fluorescent tubes.

Fluorescent lighting typically coming in long tubes for ceiling commercial fixtures and in the form of compact fluorescent lighting as a direct replacement for incandescent bulbs. Depending on the various type, brand and phosphorous, the amount of residual UV emissions may change.

UV and LED Sources

Other forms of UV sourcing can be used within this invention including UV LED. UV LED or Ultra violet light emitting diodes, are currently used in the printing industry, air filtration and other industrial areas. They provide a good UV source with minimal power input requirements. Applications within this invention may not require full spectrum lighting or visible light, thus UVLED generating a narrow UV light band spectra at or around the 388 nm wavelength would provide sufficient UV to activate the photocatalytic function of the fused nano material layer.

LED Drivers can be in the form of individual light components, sheet, or arrayed lenses. LEDS can be standard commercial LED, OLED, UV LED and blends thereof.

Other forms of integrated sources can include Plasma induction, quantum dots, and other lighting source technology that provide the potential for a full spectrum of light.

Fixtures

In commercial lighting, fluorescent bulbs are required to be covered due to potential breakage of the bulbs. In addition these covers provide a light "diffusing" function to distribute the light more evenly throughout a room.

Currently plastic diffusers are used to disperse the light from tubes. Typically these plastics are made from acrylic or polystyrene. These types of petrochemical plastics block most all of the UV spectra. Biopolymers such as polylactic acid are not petrochemically derived and have a unique molecular structure that allows for the transmission of UV frequencies through the material.

In optics, a diffuser is any device that diffuses or spreads out or scatters light in some manner, to give soft light. Diffuse light can be easily obtained by making light to reflect diffusely from a white surface, while more compact optical diffusers may use translucent objects. Commercial lighting is commonly done in healthcare, institutional, and many commercial buildings through dropped ceiling lighting. Drop ceiling lighting comprises of a metal enclosure, ballast and fluorescent tube lighting. The lighting is covered with a petrochemical plastic diffuser.

UVT Biopolymer Structures

Extruded film or sheet structures—UVT (UV transparent) biopolymer structures can be extruded into sheet or film materials that can be embossed within the extrusion process. The UVT biopolymer is melt extruded by using a sheet die at various desired thicknesses typically ranging from 0.002" to 0.5" and more commonly from 0.010" to 0.125". The extruded sheets can also comprise of various UVT fillers, fibers, and additives that are also UV transparent, but provide additional mechanical or physical properties enhancements or provide additional processing aid. Sheet are then coated Particle Fusion—UVT Particle Fusion structure are comprised of neat polylactic acid or other UV transparent biopolymer pellets wherein the pellets are formed into a layer in a mold and heated to a temperature between its melting point and its glass transition temperature. This allows the pellets to form into individual spheres, fuse together, but still maintain distinct boundary conditions. This allows the ability for unique light diffusion. The individual particles can also be coated with a transparent paint, dye of colorant and blended with various colors or clear particles as to provide a unique aesthetic design for particle fused UVT structures.

Injection or continuous shapes—Polylactic acid or other UVT biopolymers can typically be injection molded into complex 3D shapes using standard injection molding processes. UVT biopolymer molded structures can be designed into various products wherein a UV source is inside of the structure and the nanophotocatalytic layer is outside of the structure allowing UV transmission as to activate the photocatalytic function of the device.

Rotational Molded—Polylactic acid or other UVT biopolymers can be processed into a powder or fine grind and molded into a hollow shape by means of standard rotational molding. An metal mold is rotated under sufficient heat conditions as to melt the powder and coat the mold walls. Once cooled the hollow structure can be coated with the nanophotocataltic material.

These UVT biopolymer structures are all UV transparent and can also comprise of other UVT materials, fillers, polymers, and fibers as to provide a core structure for nanophotocatalytic mineral fusion on their surfaces and allowing UV transmission through the structure from a fixed and/or constant UV source.

Methods of Making

PLA processing

Blend of fluoropolymer powders with a PLA film—The blending of fine particles of fluoropolymers can act as a suspension filler with PLA extrusion in combination with the viscoelastic extrusion process for films. Generally, processing may be at temperatures sufficient to flow the PLA, but not the fluoropolymer. The film can be post treated to increase the amorphous level and clarity of the final film product. The resulting film "may" have a lower refractive index based on the blend levels of the materials. Other "high melting point" polymers can be processed into fine or nano particles that also can be processed in the same manner.

In some embodiments, various natural waxes or oils may be coupounded to modify refractive index and UV filtering or transparency function.

Nano Grinding and Spraying

Tio2 is ground into a nanosized particles and suspended in a water emulsion which can be sprayed into the surface of the UVT structures.

Fusion of Nanominerals to UVT Biopolymer Structure

The UVT Structure in the form of an extruded sheet, fused particle sheet, or molded form is preheated to a specific temperature below the melting point of the UVT biopolymer, but above the glass transition of the biopolymer. The nanomineral water emulsion is sprayed onto the surface and can be reheated to drive off residual moisture. The highly polar surface of the UVT biopolymer structure in combination with the heating provides for a firm fusion of the nanoparticles onto the active surface. The final nanocoated is heated below the melting point of the UVT biopolymer structure to assist fusing the nanoparticles onto the surface.

A lighting diffuser can be produced by extrusion method or embossing a prismatic pattern into the extruded biopolymer sheet. An alternative method is wherein pellets of UV transparent biopolymer are placed into a sheet mold or on a continuous belt and placed in an oven. The pellets are heated to a point below the melting point, but above its Tg point wherein the pellets soften and form into spherical shapes. The shapes fuse together into a sold material, but maintain independent boundaries for each spherical pellet. While still at a relatively hot condition, nanomimerals can be sprayed or coated onto the surface of the UV transparent fused panel.

A second method of applying the PCO coating to the UVT Biopolymer is wherein a UV transparent carrier liquid is added to the nanominerals and directly applied to the UVT structure. In this form of coating a alkali metal silicate can be used. The coating composition of the present invention generally includes a dispersion of photocatalysts having a mean cluster size of less than about 300 nm and an alkali metal silicate binder. The dispersion can be made by mixing the photocatalysts, a dispersant and a solvent. Preferably, the photocatalysts are transition metal oxides. Particularly preferred photocatalysts include crystalline anatase TiO2, crystalline rutile TiO2, crystalline ZnO and combinations thereof. The coating composition has a solid weight percentage of photocatalysts in the range of about 0.1% to about 90%. Preferred weight percentage is in the range of about 30% to about 80%. Examples of suitable dispersants include inorganic acids, inorganic bases, organic acids, organic bases, anhydrous or hydrated organic acid salts and combinations thereof. Suitable solvents can be any solvents that dissolve the dispersant used. Examples of suitable alkali metal silicate binders include lithium silicate, sodium silicate, potassium silicate, and combinations thereof. Applying the coating composition onto a base article, followed by heating to elevated temperatures in a oven or other suitable apparatus, produces a photocatalytic coating with improved transparency that exhibits desirable photoactivity.

Experiments

Experiment 1—Green Filtering: A modified PLA film processed using viscoelastic processing with a soybean hydrogenated wax were extruded into a 0.005" thick film. The film was then reverse printed using a solvent based inkjet printing system. A substrate of a smooth MDF and a substrates of a highly textured mineral wood composite were prepared and sprayed with a water based heat activated urethane adhesive. The thin film was low temperature formed using a vacuum forming system and fused of the surface of the composite substrate.

A second matching group of substrates were prepared and a standard PET and PVC film were applied.

The modified PLA samples fused to the substrates were evaluated by color using indoor light. The samples were taken outside into direct sunlight and a significant color shift was see wherein any printed image shifted to a very strong light green color. We believe this shows some optical or UV filter effect. We are also assuming at this time that this effect is caused due to the unique interface or chemical state at the interface of the ink and the PLA films. The PET samples were also submitted to outside light and shown no change in color.

Experiment 2—UV resistance and UV spectrophotometry: PLA has been tested for UV resistance by The Design Shop and by the primary manufacture of PLA (Cargill). Surprisingly, the UV resistance of PLA is better than the best petrochemical polymers including polycarbonate. In addition we obtained spectrophotometer work comparing a PET to a PLA showing very low to no absorbance in the UV spectra in both the UV A & B ranges as compared to high absorption with the PET in these ranges.

Experiment 3—change in crystalline and amorphous states: Although not limited to viscoelastic processing of PLA for surfacing, viscoelastic processing maintains a high degree of crystallinity within the PLA films. Viscoelastic processing integrates lower temperature processing or modified temperature profiles in combination with various additives including hydrogenated soybean wax that maybe acting as a nucleating agent. The resulting film is semitransparent, but also has a unique optical effect that highlights the decorative printing patterns of our material. In further, post processing such as thermofoiling, we see a definite change in clarity at 140 F to 180 F wherein, the Biolaminate film increases its clarity significantly. This can be adjusted by adjusting the range and processing parameters of thermofoiling.

Experiment 4—Polylactic acid pellets from Natureworks were placed into a mold and heated to its melting temperature under pressure creating a thin sheet. A second sheet was produced by means of standard extrusion processing. The material samples were subjected to photospectrometer tests. The results showed that the material transmitted UV frequencies into the UV A and UV B frequencies at high levels of UV transmission (over 90%) at the targeted 388 nano meter range.

Experiment 5—Polylactic acid pellets were layered into a sheet mold two pellets in depth. The mold was placed in an oven at 340 F for 8 minutes. The pellets first became "spherical" as they reach their softening point, but below their melt point. The pellets fused together and once cooled became a solid sheet of high integrity. The individual pellets were all in a spherical shape. The panel was then placed in a light fixture and compared to a standard acrylic light diffuser (crystal pattern). The light from the PLA sphere panels was highly dispersed at all angles whereas the standard acrylic panel shown a strong focus in the middle and quickly lowered in light intensity as the angle of your eye decreased.

Experiment 6—Cellulose acetate and polylactic acid were individually extruded into a sheet and measured for its UV transmission at 388 nm in comparison to acrylic. The acrylic was less than 10% transmission at this UV spectra whereas the PLA and cellulose acetate shown a very high degree of transmission greater than 90%.

Experiment 7—Nanoquartz was blended with PLA at a level of 10% by weight and extruded into a sheet sample. The sample was submitted to photospectroscopy. The material shown the same UV transparency as the neat PLA comparison sample with minimal loss in the UV A spectra.

Experiment 8—Nanoquartz mineral was coated over the surface of a polylactic acid sheet. The material was heated to a temperature above its Tg and below it melting point. The part was cooled. In using a brush on the surface to attempt to remove the quartz. Little to no quartz was removed from the surface.

Experiment 9—nanoTio2 photocatalytic mineral was coated on the top surface of an extruded PLA sheet. A UV light source was placed on the opposite backside of the PLA sheet. Smoke was blown into a container and placed on top of the PLA sheet. The photocatalytic reaction with UV light transferring through the UV transparent PLA reduced and eliminated the smoke in a matter of minutes.

What is claimed is:

1. An ultraviolet transparent (UVT) biopolymer photocatalytic system comprising:
    an ultraviolet transparent (UVT) biopolymer photocatalytic structure; and
    a UV source:
    wherein the structure comprises a UVT biopolymer layer, comprising polylactic acid and having a surface; and a nanophotocatalytic layer arranged on the surface of the UVT biopolymer layer; and
    wherein the structure is arranged and oriented relative to the UV source such that light in a UV spectra from the UV source reaches the UVT biopolymer layer, passes through the UVT biopolymer layer, and activates the nanophotocatalytic layer.

2. The UVT biopolymer photocatalytic system of claim 1, wherein the UV source is a fluorescent bulb.

3. The UVT biopolymer photocatalytic system of claim 1, wherein the UV source is a UV light emitting diode.

4. The UVT biopolymer photocatalytic system of claim 1, wherein the UV source is direct sunlight.

5. The UVT biopolymer photocatalytic system of claim 1, further comprising a filler in one of the UVT biopolymer layer or the nanophotocatalytic layer.

6. The UVT biopolymer photocatalytic system of claim 5, wherein the filler is fused quartz.

7. The UVT biopolymer photocatalytic system of claim 5, wherein the filler is sapphire.

8. The UVT biopolymer photocatalytic system of claim 5, wherein the filler is nanosilica.

9. The UVT biopolymer photocatalytic system of claim 1, further comprising glass in one of the UVT biopolymer layer or the nanophotocatalytic layer.

10. The UVT biopolymer photocatalytic system of claim 1, wherein activation of the nanophotocatatlytic layer reduces ambient bacteria, viruses, VOC, or odors.

* * * * *